United States Patent
Dittmer et al.

(10) Patent No.: US 9,720,003 B2
(45) Date of Patent: Aug. 1, 2017

(54) ASSAY FOR TROPONIN I USING MAGNETIC LABELS

(75) Inventors: Wendy Uyen Dittmer, Eindhoven (NL); Toon Hendrik Evers, Eindhoven (NL); Peggy De Kievit, Eindhoven (NL); Ricky Kamps, Eindhoven (NL); Joost Lambert Max Vissers, Nijmegen (NL); Michael Franciscus Wilhelmus Cornelis Martens, Helmond (NL); David Walterus Cornelis Dekkers, Veldhoven (NL)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 815 days.

(21) Appl. No.: 13/141,439

(22) PCT Filed: Dec. 15, 2009

(86) PCT No.: PCT/IB2009/055757
§ 371 (c)(1),
(2), (4) Date: Jun. 22, 2011

(87) PCT Pub. No.: WO2010/073182
PCT Pub. Date: Jul. 1, 2010

(65) Prior Publication Data
US 2011/0256640 A1 Oct. 20, 2011

(30) Foreign Application Priority Data
Dec. 22, 2008 (EP) ..................................... 08172611

(51) Int. Cl.
*G01N 33/68* (2006.01)
*G01N 33/543* (2006.01)

(52) U.S. Cl.
CPC ... *G01N 33/6887* (2013.01); *G01N 33/54373* (2013.01); *G01N 2800/324* (2013.01)

(58) Field of Classification Search
CPC ......... G01R 33/1269; G01N 33/54326; G01N 27/745
See application file for complete search history.

(56) References Cited

U.S. PATENT DOCUMENTS

| 4,336,173 A | 6/1982 | Ugelstad |
| 4,459,378 A | 7/1984 | Ugelstad |
| (Continued) | | |

FOREIGN PATENT DOCUMENTS

| EP | 1798504 A1 | 6/2007 |
| WO | 9419690 A1 | 9/1994 |
| (Continued) | | |

OTHER PUBLICATIONS www.antibodies-online.com web page, downloaded Mar. 7, 2017.*
(Continued)

*Primary Examiner* — Melanie Y Brown
*Assistant Examiner* — Richard Moerschell

(57) ABSTRACT

The present invention relates to a method for measuring Troponin I in a sample comprising the steps of providing a sample, contacting the sample with a monoclonal anti-Troponin I antibody coupled to a magnetic label, contacting the sample with a polyclonal anti-Troponin I antibody coupled to a sensor surface and detecting the magnetic label on the sensor surface. The invention further relates to a device and a cartridge for measuring Troponin I in a sample.

5 Claims, 2 Drawing Sheets

(56) References Cited

U.S. PATENT DOCUMENTS

| | | | |
|---|---|---|---|
| 4,654,267 | A | 3/1987 | Ugelstad |
| 5,350,676 | A | 9/1994 | Oberhardt |
| 5,604,105 | A * | 2/1997 | Jackowski .................... 435/7.4 |
| 6,569,634 | B1 * | 5/2003 | Hoshino et al. ............ 435/7.23 |
| 6,673,628 | B2 | 1/2004 | Freitag et al. |
| 7,425,455 | B2 | 9/2008 | Fukumoto et al. |
| 9,267,939 | B2 | 2/2016 | Campbell et al. |
| 2001/0019405 | A1 * | 9/2001 | Herron et al. ................. 356/39 |
| 2002/0072590 | A1 * | 6/2002 | Van Eyk et al. ............. 530/412 |
| 2002/0102620 | A1 * | 8/2002 | Maret et al. ................ 435/7.22 |
| 2002/0197741 | A1 | 12/2002 | Sabucedo |
| 2003/0082658 | A1 * | 5/2003 | Mallet et al. ............... 435/7.92 |
| 2004/0018577 | A1 * | 1/2004 | Emerson Campbell et al. ........................... 435/7.93 |
| 2005/0124077 | A1 * | 6/2005 | Cole et al. ................... 436/518 |
| 2006/0024756 | A1 * | 2/2006 | Tibbe et al. .................. 435/7.2 |
| 2009/0061455 | A1 * | 3/2009 | Sankaran et al. .............. 435/7.1 |
| 2010/0009456 | A1 * | 1/2010 | Prins et al. .................. 436/164 |
| 2014/0141484 | A1 * | 5/2014 | Campbell et al. ............ 435/188 |

FOREIGN PATENT DOCUMENTS

| | | | |
|---|---|---|---|
| WO | 9964868 | A1 | 12/1999 |
| WO | 2007114947 | A2 | 10/2007 |
| WO | 2007129275 | A2 | 11/2007 |
| WO | 2007132373 | A1 | 11/2007 |
| WO | WO 2007/129275 | * | 11/2007 ............. G01R 33/12 |

OTHER PUBLICATIONS

De Boer, B.M. et al "An Integrated and Sensitive Detection Platform for Magneto-Resistive Biosensors" Sciencedirect Biosensors and Bioelectronics, vol. 22, 2007, pp. 2366-2370.

Jingyan Wei et al., Detection of cardiac troponin I in sera with surface Plasmon resonance biosensor, Chinese Journal of Immonology, vol. 20, No. 4, pp. 272-275. Apr. 20, 2004 (No Translation Available).

* cited by examiner

ASSAY FOR TROPONIN I USING MAGNETIC LABELS

FIELD OF THE INVENTION

The present invention relates to a method, a device and a cartridge for measuring Troponin I in a sample. The invention further relates to the use of this method, device and cartridge in a process of diagnosing myocardial infarction.

BACKGROUND OF THE INVENTION

Measurement of Troponin I in blood is an important step in the diagnosis of a myocardial infarction.

State-of-the-art biological analysis of Troponin I is based on laboratory high-sensitivity heterogeneous immunoassays with luminescence detection. This involves the emission of light from a chemical reaction, or the visualization of an emitting label. Using such immunoassays results in immunoassay sensitivities in the order of pg/mL. Generally, these assays are performed on large automated detection systems designed for high throughput measurements and are not suitable for rapid testing outside of centralized laboratories by non-technical users.

Immunoassays that use magnetic labels as detection labels are known in the prior art. Such assays enable magnetic actuation and reduce the assay time. In these assays, magnetic labels are sterically hindered due to their large dimensions and do not bind to a surface with molecular receptors as easily as molecular labels (such as radioactive iodine, enzymatic label etc.). Moreover, because labels are magnetized during the assay, the duration of contact between labels increases, which enhances the probability that the magnetic labels irreversibly aggregate and quantitative information is lost. This can be a significant problem when larger magnetic particles (>200 nm) are used as they are more prone to form irreversible clusters.

SUMMARY OF THE INVENTION

It is an object of the present invention to provide a sensitive and rapid method for measuring Troponin I in a sample. The object is realized by a method for measuring Troponin I in a sample comprising at least the following steps:
Providing a sample
Contacting the sample with a monoclonal anti-Troponin I antibody coupled to a magnetic label
Contacting the sample with a polyclonal anti-Troponin I antibody coupled to a sensor surface, or at least two different anti-Troponin I antibodies coupled to a sensor surface
Detecting the magnetic label on the sensor surface, wherein steps b and c can be performed in any order.

Hereinafter "polyclonal anti-Troponin I antibody is meant to include both polyclonal anti-Troponin I antibody and at least two different antibodies against Troponin I.

"In any order" includes the simultaneously contacting of the sample with the monoclonal and polyclonal anti-Troponin I antibody.

Preferably, step b precedes step c. This sequence of steps improves the assay binding as the monoclonal anti-Troponin I antibody coupled to a magnetic label has more degrees of freedom relative to the polyclonal anti-Troponin I antibody coupled to the sensor surface. This embodiment leads to decreased assay times.

The present invention provides a fast immunoassay test for Troponin I that permits the sensitive detection of Troponin I within 5 minutes using a small sample volume. The binding of labels of a relatively large size to a bulk sensor surface is a challenge due to the reduced mobility of both the primary and secondary antibody that is attached to their respective surfaces.

Antibodies for Troponin I that function well in solution and that are recommended by antibody suppliers, do not yield high signals in the 1-step magnetic label assay. Without wishing to be bound by this theory, the reason for this is likely due to more severe requirements for the antibodies to be optimally oriented for binding in the magnetic label assay.

The combination of a monoclonal anti-Troponin I antibody coupled to a magnetic label with a polyclonal anti-Troponin I antibody coupled to the sensor surface gives improved results compared to the suppliers' data sheet recommended antibody couples for Troponin I assays.

In a preferred embodiment, the magnetic label is a particle comprising inorganic material or a combination of inorganic and organic material e.g. iron oxide grains in a polymer matrix. The use of magnetic labels enables magnetic actuation, speeding up the reaction kinetics of the assay. Moreover, the use of magnetic labels facilitates removal of any label, bound or unbound to the monoclonal anti-troponin I antibody, that is not complexed to the sensor surface via a magnetic field preferably in combination with a gradient. This embodiment abolishes the need for additional washing steps to identify specific signal versus background binding.

In a preferred embodiment, the magnetic label used has a size of 200 to 1000 nm. Particles in this size range allow for optimal assay conditions and detection.

In another preferred embodiment, the polyclonal anti-Troponin I antibody used is a goat polyclonal anti-Troponin I antibody. The use of goat polyclonal antibodies leads to optimized assay results.

In another embodiment, the magnetic label is optically detected, preferably by frustrated total internal reflection (FTIR). In yet another embodiment, the magnetic label is magnetically detected.

Additionally or alternatively it is envisaged that magnetic labels can be detected based on the presence of a second, either magnetic or non-magnetic label. This label can be either directly attached to the magnetic label or indirectly bound to the label through an analyte. A non-magnetic label can be attached to a magnetic label via an inorganic or organic component at the outside of the magnetic label or can be incorporated into the magnetic label. Suitable second labels in the context of the present invention are those labels which are classically used in in vitro assays such as, but not limited to, chromophoric groups, radioactive labels, electroluminescent labels, chemiluminescent labels, phosphorescent labels, fluorescent labels or reflecting labels.

The object of the invention is further realized by a biosensor device capable of measuring Troponin I according to the method of the present invention.

Furthermore, the object of the invention is realized by a cartridge for use in an assay device, comprising:
a monoclonal anti-Troponin I antibody bound to a magnetic label
a polyclonal anti-Troponin I antibody bound to a sensor surface within the cartridge
a sample inlet.

Preferably, the magnetic label in the cartridge has of a size of 200 to 1000 nm.

In a preferred embodiment of the cartridge, the polyclonal anti-Troponin I antibody is a goat polyclonal antibody.

The present invention will be described with respect to particular embodiments and with reference to certain drawings but the invention is not limited thereto. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

DETAILED DESCRIPTION OF THE INVENTION

The present invention discloses a method for the detection of Troponin I, preferably mammalian Troponin I, more preferably, human Troponin I via an immunoassay.

Figure 1A:
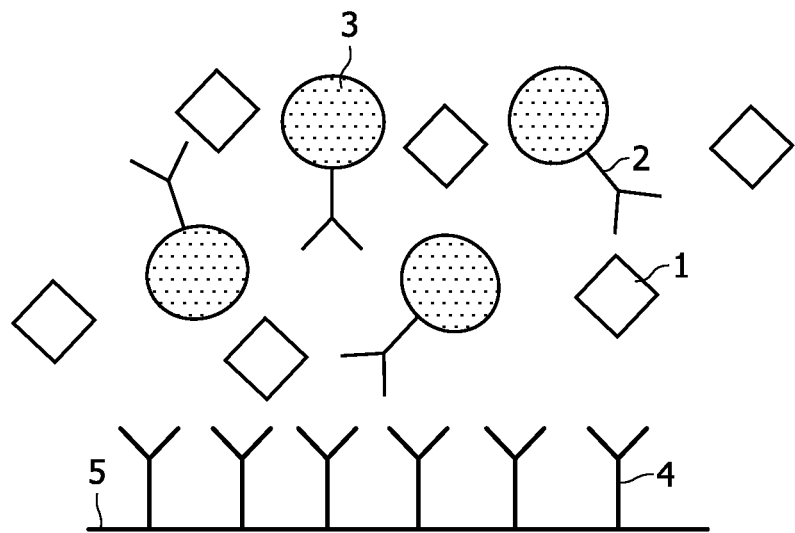
FIG. 1: Schematic representation of the assay according to the invention
Figure 1B:
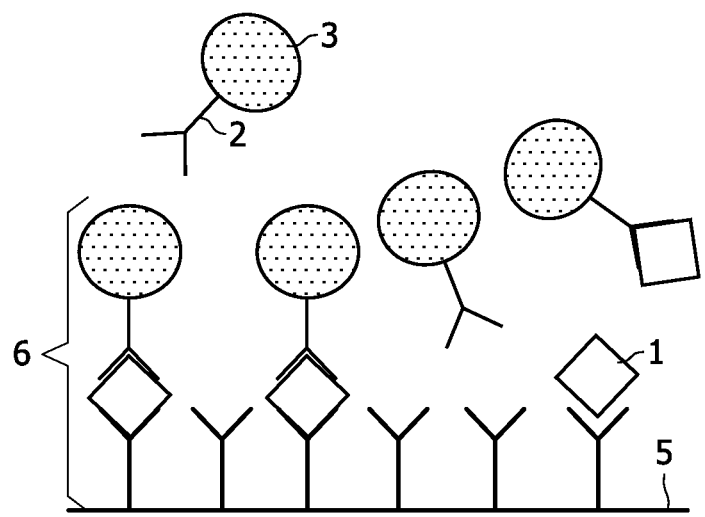
Figure 2:
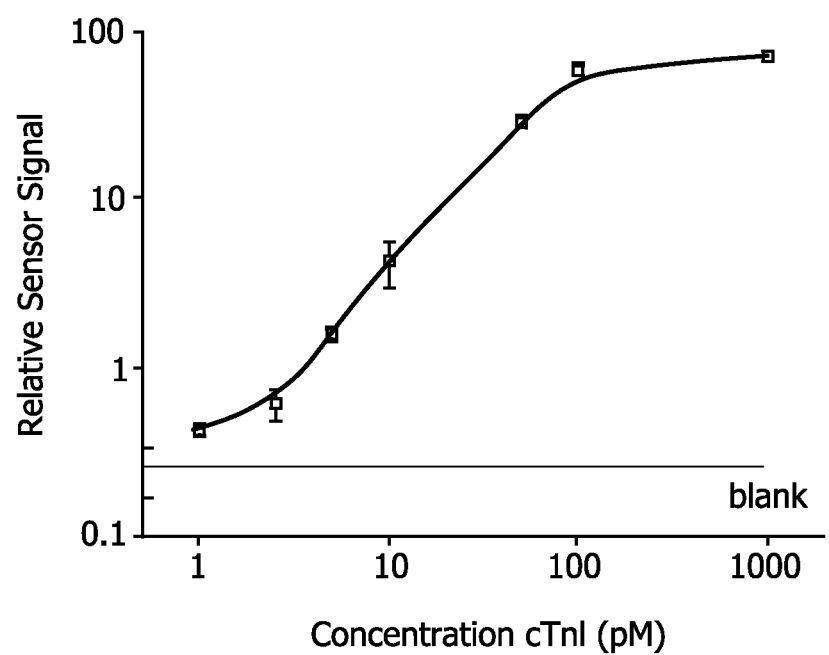
FIG. 2: Dose response curve of Troponin I

The assay uses two different antibodies, a monoclonal anti-Troponin I antibody coupled to a magnetic label and a polyclonal anti-Troponin I antibody coupled to a sensor surface. FIG. 1 shows a schematic setup of an assay according to the invention. In FIG. 1A a sample potentially comprising Troponin I (1) is contacted with monoclonal anti-Troponin I antibodies (2) coupled to a magnetic label (3). The sample is additionally contacted with polyclonal anti Troponin I antibodies (4) coupled to a sensor surface (5). The monoclonal and polyclonal anti-Troponin I antibodies are selected such that the analyte of interest, i.e. in the present case Troponin I, can be bound to both the monoclonal and polyclonal anti-Troponin I antibody simultaneously. If Troponin I is present in the sample, complexes (6) will be formed on the sensor surface that consist of the polyclonal antibody coupled to the sensor surface, Troponin I and the monoclonal antibody coupled to a magnetic label. This is schematically shown in FIG. 1B. Preferably after removing the monoclonal anti-Troponin I antibody comprising the magnetic label, or any bare magnetic label, that is not specifically complexed to the surface via Troponin I, the amount of Troponin I present on the sensor surface is determined. The elements of the present invention will be described in the following sections.

Antibodies

The monoclonal antibody according to the present invention also includes Fab fragments from monoclonal antibodies, aptamers, affibodies, scFv fragments and any other single epitope binding moiety known to the person skilled in the art. The polyoclonal antibody according to the present invention also includes Fab fragments from polyclonal antibodies, and any group of binding moieties with variable structure known to the person skilled in the art.

In a preferred embodiment the antibody according to the present invention is directed at amino acid sequence 30-110, more preferably 80-110, of the Troponin I molecule. This is the stable part of the molecule. Preferably the epitopes chosen do not overlap with known regions for heparin binding which would result in interference from heparinized samples.

Preferably, the monoclonal anti-Troponin I antibody is selected from the group comprising clones A34500 (binding to amino acid 87-91 of Troponin I), 81-7 (a34780 binding to amino acid 136-154 of Troponin I), A34650 (binding to amino acid 41-49 of Troponin I), 267 (ab 14530, binding to amino-acid 169-184 of Troponin I), 16A11 (a24460, binding to amino-acid 87-91 of Troponin I), 19C7 (a19615, binding to amino-acid 41-49 of Troponin I), 560 (binding to amino acid 83-93 of cTnI) or combinations thereof.

The use of these clones leads to improved selectivity in the magnetic immunoassay according to the invention.

Coating procedures are specific to the magnetic labels that are used in the assay. The Ademtech protocol, known for a person skilled in the art can be used. In this protocol, monoclonal antibody at a concentration of for example 20 ug antibody/mg magnetic label is coupled to carboxylated magnetic labels in the presence of EDC (1-Ethyl-3-(3-dimethylaminopropyl)-carbodiimide).

The sensor surface according to the present invention is functionalized with polyclonal antibodies. Polyclonal antibodies are preferred as the degrees of freedom for binding of Troponin I, especially when bound to the monoclonal anti Troponin I antibody with the magnetic label are limited. One advantage is a consequence of the variability in orientation of polyclonal antibodies immobilized on a surface due to the different antibody types of a polyclonal. Further advantages can arise by increasing the amount of suitable binding sites by using polyclonal antibodies directed to different epitopes leading to optimized assay results.

Due to favorable results, polyclonal goat antibodies specific for Troponin I are more preferred.

In yet another embodiment, an additional antibody specific for Troponin I, or a mixture of several antibodies specific for Troponin I is coated on the sensor surface. Preferably the additional antibody is a monoclonal antibody.

In another embodiment of the invention, the surface is coated with at least two, even more preferably at least 3, different monoclonal anti-Troponin I antibodies or a mixture of monoclonal troponin I antibodies. This also leads to a "polyclonal" antibody surface on the receptor, as binding sites for more than one epitope are present. This situation functionally resembles the coating of a polyclonal antibody.

The antibody can for example be coated on the sensor surface by inkjet printing a drop (of e.g. 2 nL) at a concentration of about 150 ug/mL in PBS.

Magnetic Label

In the present invention, monoclonal anti-Troponin I antibody is coupled to a magnetic label comprising magnetic elements that allow manipulation of the labeled antibody via a magnet in an assay device.

The nature of the magnetic labels used in the context of the present invention is not critical. Suitable magnetic labels include completely inorganic labels and labels which are a mixture of an inorganic and an organic material (e.g. a polymer).

Magnetic labels are commercially available from e.g. Dynal, Estapor, Seradyn and are widely used in biological analysis that are available from several diagnostic companies.

Attachment of the monoclonal anti-Troponin I antibody according to the invention to the surface of a magnetic label can be performed by methods described in the art. For instance, the magnetic label may carry one or more functional groups such as hydroxyl, carboxyl, aldehyde or amino groups. These may in general be provided, for example, by treating uncoated monodisperse, superparamagnetic labels, to provide a surface coating of a polymer carrying one of such functional groups, e. g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many of such surface coatings. Other coated magnetic labels may be prepared by modification of the labels according to the U.S. Pat. No. 4,336,173, U.S. Pat. No. 4,459,378 and U.S. Pat. No. 4,654,267. For example, macroreticular porous polymer particles, prepared from styrene-divinylbenzene and with a diameter of 3.15 µm, can be treated with $HNO_3$ to introduce-$NO_2$ groups at the surface of the pores. Then the particles can be dispersed in an aqueous solution of Fe. The $Fe^{2+}$ is oxidized by the $NO_2$ groups which leads to precipitation of insoluble iron oxy-hydroxy compounds inside the pores. After heating the iron exists as finely divided grains of magnetic iron oxides throughout the volume of the porous particles. The $NO_2$ groups are reduced by the reaction with Fe to $NH_2$ groups. To fill up the pores and to introduce the desired functional groups at the surface, different monomers are caused to polymerize in the pores and at the surface. In the case of a preferred type of particle, the surface carries OH groups connected to the polymeric backbone through $(CH_2CH_2O)_{8-10}$ linkages. Other preferred particles carry —COOH groups obtained through polymerization of methacrylic acid. For example, the $NH_2$ groups initially present in the particles may be reacted with a di-epoxide as described in U.S. Pat. No. 4,654,267, followed by reaction with methacrylic acid to provide a terminal vinyl grouping. Solution copolymerization with methacrylic acid yields a polymeric coating carrying terminal carboxyl groups. Similarly, amino groups can be introduced by reacting a diamine with the above product of the reaction with a diepoxide, while reaction with a hydroxylamine such as aminoglycerol introduces hydroxy groups. The coupling of a bioactive molecule to a particle can be irreversible but can also be reversible by the use of a linker molecule for the crosslinking between label and bioactive molecule. Examples of such linkers include peptides with a certain proteolytic recognition site, oligonucleotide sequences with a recognition site for a certain restriction enzyme, binding partners such as streptavdin/biotin, or chemical reversible crosslinking groups as those comprising a reducible disulfide group. A variety of reversible crosslinking groups can be obtained from Pierce Biotechnology Inc. (Rockford, Ill., USA).

Magnetic labels are commercially available in various sizes, ranging from nanometers to micrometers.

When considering the magnetic label size to employ in a high sensitivity assay, it is important to weight the counteracting effects. The larger the label the higher is the signal per binding event. Moreover, large magnet labels imply larger magnetic content which in turn allow a large force to be applied for a given magnetic field. This permits the labels to be collected and moved through the solution with a greater speed. On the other hand large magnetic labels have a tendency to irreversibly aggregate and are more sterically hindered when they bind to a surface. In addition, large label reduce the dynamic range and the quantitivity of the assay, as the packing number of labels on the sensor surface is limited for larger labels. For high sensitivity and high speed we find the optimal magnetic label size to be between 200 and 1000 nm. With 500 nm magnetic labels we are able to obtain 1 pM LOD with a 5 minute assay according to the invention.

Detection

The term "sensor surface" as used herein refers to a surface to which antibodies can be coupled and which allows the detection of a label in its vicinity. Typically, the detection surface is a solid, uniform surface. The detection surface can be a sensor surface, i.e. a surface which is involved in detection. Alternatively, the sensor can be located in the vicinity e.g. under the detection surface, allowing detection of labels present close to the detection surface.

Detection of the Troponin I concentration in a sample with different detection techniques is illustrated, the present invention not being limited thereto.

The detection surface to which the polyclonal anti-Troponin I antibodies are bound in devices used in the methods of the invention is typically a specially derivatized surface to which molecules, more particularly antibodies or functional fragments thereof can be bound. Examples of suitable surfaces include, glass, metal, plastic, an organic crystal or an inorganic crystal (e. g. silicon), an amorphous organic or an amorphous inorganic material (e. g. silicon nitride, silicon oxide, silicon oxinitride, aluminum oxide). Suitable surface materials and linking chemistries are known to the person skilled in the art, and are described for instance in "Diagnostic Biosensor Polymers", by A. M. Usmani and N. Akmal, American Chemical Society, 1994 Symposium Book Series 556, Washington D.C., USA, 1994, in "Protein Architecture, Interfacing Molecular Assemblies and Immobilization Biotechnology", edited by Y. Lvov and H. Mhwald (Marcel Dekker, New York, 2000), in "The Immunoassay Handbook" by David Wild (Nature Publishing Group, London, 2001, ISBN 1-56159-270-6) or "Handbook of Biosensors and Electronic Noses. Medicine, Food and the Environment" by Kress-Rogers (ISBN 0-8493-8905-4). Supports for coupling proteins to coated and uncoated plastic and glass supports are disclosed in Angenendt et al. (2002; *Anal Biochem.* 309, 253-260).

Detection means suitable for use in the methods, systems and devices of the present invention are detection means capable of detecting the relevant signal such as, but not limited, to a magnetic signal, magnetoresistance, a Hall effect, an optical signal (reflection, absorption, scattering, fluorescence, chemiluminescence, RAMAN, FTIR, etc.). Such optical labels are known to the skilled person and include fluorescein dyes, such as 5- (and 6-) carboxy-4',5'-dichloro-2',7'-dimethoxy fluorescein, 5-carboxy-2',4',5',7'-tetrachlorofluorescein and 5-carboxyfluorescein, rhodamine dyes such as 5- (and 6-) carboxy rhodamine, 6-carboxytetramethyl rhodamine and 6-carboxyrhodamine X, phthalocyanines such as methyl, nitrosyl, sulphonyl and amino phthalocyanines, azo dyes, azomethines, cyanines and xanthines such as the methyl, nitro, sulphano and amino derivatives, and succinylfluoresceins. Other suitable labels are fluorophores from the group of cyanine dimers and monomers, such as TOTO, YOYO, TO-PRO, Cy3, Cy5, Cy5.5, Cy7 etc., or dyes such as LCRed 705 may be used as the fluorescent dye.

In particular embodiments detection means are capable of detecting an acoustical signal (quartz crystal microbalance (QCM), surface acoustic waves (SAW) or Bulk Acoustic Wave (BAW) etc.). Such acoustic signals may be generated by vesicles such as liposomes, micelles, or bubbles. Such vesicles may be filled with a liquid, a gas, a gaseous precursor, and/or a solid or solute material.

Depending on the nature of the signal to be detected, the detection surface can be an integral part of the detection means (sensor surface) or can allow the detection of the presence of magnetic labels on its surface.

In one example, radioactive labels, such as e g luminescent or fluorescent labels, are embedded in or attached to the labels that are used. Excitation of the fluorescent labels can be done using an irradiation source, such as for example via a focused laser beam or via evanescent field excitation allowing optical detection of such labels. Detection can be done in any suitable way, such as for example using confocal detection or using a high-NA lens. The use of fluorescent labels enables multiplexing by using different fluorophores, which differ in excitation and/or emission wavelengths.

Optical detection can be done also by Surface-Enhanced Resonance Raman spectroscopy (SERRS). SERRS is an ultra-sensitive method for detection of molecules or species by adsorption of the molecule or species that is optically labeled on colloidal labels, e.g. silver particles. The optical label is a suitable dye molecule (such as Rhodamine) causing plasmon and dye resonance when the colloidal particles cluster in a controlled way. It is known that for example magnetic labels exist with a metallic coating. If for example antigens (to which the target, i.e. antibodies, binds) are coupled to such silver-coated magnetic label, while the antigens are also coupled to a suitable dye, antigen-specific antibodies will lead to linking of the dye to the silver-coated magnetic labels. Magnetic actuation will lead to cluster/pillar formation which will lead to dye resonance. SERRS can be detected after actuation to a non-binding sensor surface in an evanescent field. In such a set-up, antibody detection can be done in a single chamber omitting fluid wash steps since the detection is surface specific and not disturbed by unbound dyes from solution.

In another example, a magnetic sensor may be used, such as for example a Hall sensor, a magnetoresistive sensor such as for example an GMR, TMR or AMR sensor. In a particular example, the magnetic sensing may take advantage of the fact that a particular frequency may be used for the applied AC magnetic field. In the low frequency regime, i.e. at frequencies e.g. below 100 Hz, the 1/f noise of the magnetic sensor element dominates. 1/f noise is caused by point-to-point fluctuations of the current and is proportional to the inverse of the frequency. In magnetoresistive sensors, 1/f noise originates from magnetic fluctuations in the free layer. When the frequency of the generated AC magnetic field is 100 Hz or above, the dominating 1/f noise is significantly reduced compared to the prior art, resulting in an improved signal to noise ratio (SNR). It is advantageous when the frequency of the AC magnetic field is further increased to a value where the thermal white (Nyquist) noise level becomes dominant over the 1/f noise level. As mentioned in WO 2005/010542, above a certain corner frequency $f_c \approx 50$ kHz the thermal white noise of GMR sensors becomes dominant. The white-noise level limits the theoretically achievable detection limit As mentioned above the detection of magnetic labels at a detection surface can be ensured by any direct or indirect method known in the art. Particular detection methods are based on the magnetic properties of the label such as GMR or on optical properties of the magnetic labels, such as detection with frustrated total internal reflection (FTIR). Miniaturised GMR sensor chips, integrated in disposable flow-cell cartridges, as described in e.g. Nellissen et al. (2007) in proceedings of the 15th European Microelectronics and Packaging Conference p 210-204, or in De Boer et al. (2007) Biosens. Bioelectron. 22, 9-10, are suitable for performing the methods of the present invention, and can detect a label density of three 300 nm labels on a 1500 $\mu m^2$ chip surface.

Cartridge

In an embodiment of the invention, the monoclonal anti-Troponin I antibody bound to the magnetic label and the polyclonal anti-Troponin I antibody bound to the sensor surface are present within a cartridge. As the reagents for the assay are already present within the cartridge, the user only needs to add the sample fluid via the sample inlet, which redisperses the reagents and labels to produce the intended buffer conditions. The dry reagents preferably include the buffer components necessary for the assay and the magnetic labels with the monoclonal anti Troponin I antibodies. The components of the dry reagents can be deposited and dried individually at different location in the cartridge or together at the same location. The reagents can be deposited via several drying techniques including lyophilization. Lyophilization prevents the formation of crystals and allows the reagents to be dried to an amorphous glassy state that is readily redispersed upon the addition of a fluid. The cartridge preferably is suitable for optical detection of the magnetic labels.

Biosensor Device

According to an embodiment of the invention, the presence or concentration of Troponin I in a sample is determined by using a biosensor device. The biosensor device should comprise a reaction chamber for contacting the sample with monoclonal anti-Troponin I antibody coupled to a magnetic label and polyclonal anti-Troponin I antibody coupled to a sensor surface. In this chamber, binding of Troponin I to both the monoclonal anti-Troponin I antibody coupled to a magnetic label and polyclonal anti-Troponin I antibody coupled to a sensor surface with Troponin I should be facilitated.

The reaction chamber preferably is part of a cartridge to facilitate easy use of the biosensor device.

In particular embodiments of the method described in the present invention, the optimization of antigen-antibody interaction is achieved by magnetic actuation; applying a magnetic field directed towards the detection surface and/or pulsed actuation forces to the magnetic labels carrying the first anti-Troponin I antibodies during the assay to ensure optimized contact with the detection surface. Magnetic labels can be manipulated in different ways to optimise contact with the immobilized antibodies. In particular embodiments, magnetic actuation in the assay is performed as follows.

In a first step, the labels with the monoclonal antibody are rapidly attracted to the sensor surface in a "collection" step. This is ensured by applying a magnetic field in the direction of the sensor surface. In particular embodiments the magnetic field ensures that the magnetic labels have reached the sensor surface, for instance such as to reach at least 50%, 75% or 90% of monolayer formation on the surface, preferably 100% monolayer formation.

In a second step, the magnetic forces are removed and the labels are allowed to move over the surface with essentially unhindered translational as well as rotational degrees of freedom. After a certain time diffusion occurs and, in particular embodiments it is envisaged that the oriented magnetic field of the first step is once again applied. These steps can be repeated several times to ensure that all magnetic labels with Troponin I bound to the monoclonal antibodies are bound to the polyclonal antibody on the detection surface. By this alternation of on/off of the magnetic field, pulsed actuation is obtained.

In alternative embodiments of the magnetic actuation conditions envisaged herein, the rotation and translation at the detection surface is not merely a result of passive diffusion in the absence of a magnetic field, but is actively ensured by the application of one or more magnetic fields which ensure the movement of magnetic labels over the detection surface.

In particular embodiments the magnetic force enabling the movement of magnetic labels over the detection surface is ensured by pulsed actuation of the labels. This can involve e.g. alternating the direction of a magnetic field perpendicular to the detection surface or parallel to the detection surface or a combination of different fields with different orientations. Such methods are described e.g. in WO2007129275. The time and duration of each pulse is designed based on the label size so as to optimally allow the label to undergo at least one full rotation over its axis over the binding surface. In particular embodiments, the actuation forces are essentially perpendicular to the surface as strong forces parallel with the sensor surface can remove specifically bound magnetic labels.

In methods described herein it is optionally envisaged that, after the contacting of the magnetic labels with the detection surface through magnetic actuation, a magnetic force is applied directing the labels away from the detection surface to ensure the removal of unbound labels. In this way additional washing steps for removal of the magnetic label are no longer necessary.

It has been found that methods involving pulsed actuation alternated with translational and rotational movement of magnetic labels on the detection surface are significantly more efficient than methods which involve only a constant magnetic force attracting the labels to the detection surface. The pulsed actuation also reduces the probability that labels irreversibly aggregate as the amount of time that the labels are in contact with one another is also reduced.

A preferred actuation scheme consists of about 1 minute incubation of the sample with the cartridge and magnetic labels followed by about 4 minute pulsed actuation and about 10 second label removal with a top coil.

Sample

The term "sample" is used in a broad sense herein and is intended to include a wide range of biological materials as well as compositions derived or extracted from such biological materials. The sample may be any suitable preparation in which the target Troponin I is to be detected, preferably blood. The sample may comprise, for instance, a body tissue or fluid such as but not limited to blood (including plasma and other fractions), spinal fluid, mucus, sputum, saliva, semen, stool or urine or any fraction thereof. Exemplary samples include whole blood, red blood cells, white blood cells, buffy coat, hair, nails and cuticle material, swabs, including but not limited to buccal swabs, throat swabs, vaginal swabs, urethral swabs, cervical swabs, rectal swabs, lesion swabs, abscess swabs, nasopharyngeal swabs, nasal swabs and the like, lymphatic fluid, amniotic fluid, cerebrospinal fluid, peritoneal effusions, pleural effusions, fluid from cysts, synovial fluid, vitreous humor, aqueous humor, bursa fluid, eye washes, eye aspirates, plasma, serum, pulmonary lavage, lung aspirates, biopsy material of any tissue in the body. The skilled artisan will appreciate that lysates, extracts, or material obtained from any of the above exemplary biological samples are also considered as samples. Tissue culture cells, including explanted material, primary cells, secondary cell lines, and the like, as well as lysates, extracts, supernatants or materials obtained from any cells, tissues or organs, are also within the meaning of the term biological sample as used herein. These lists are not intended to be exhaustive.

In particular embodiments of the invention, the sample is pre-treated to facilitate the detection of the sample with the detection method. For instance, typically a pre-treatment of the sample resulting in a semi-isolation or isolation of the target Troponin I is envisaged. Many methods and kits are available for pre-treating samples of various types.

Particular embodiments of the present invention relate to methods wherein one or more of the different conditions for optimising detection of Troponin I are combined. In further particular embodiments all of the above-described conditions improving the detection of Troponin I are combined.

Other arrangements of the device, cartridge and methods embodying the invention will be obvious for those skilled in the art.

It is to be understood that although preferred embodiments, specific constructions and configurations, as well as materials, have been discussed herein for devices and cartridges according to the present invention, various changes or modifications in form and detail may be made without departing from the scope and spirit of this invention.

EXAMPLES

A dose response curve was determined for Troponin I by using the method according to the invention. Results are shown in FIG. 3. The polyclonal anti-Troponin I antobody used in the cartridge is a goat polyclonal antibody that has been inkjet printed on to the polymer sensor surface at a concentration of 150 ug/mL antibody in PBS. 500 nm COOH magnetic labels are iron oxide particles with a particle coating from Ademtech SA functionalized with a solution of 20 ug A34780(359P), clone 8I-7, antibody/mg magnetic particle and diluted in 5% BSA in PBS. Troponin I standards (Hytest 8T62) were diluted in 40% human serum in PBS. The magnetic label and Troponin I solutions were diluted 1:1 and 1 uL was exposed to the sensor surface. An actuation protocol consisting of 4 minute pulsed actuation and 10 s label removal with a top coil was used.

The invention claimed is:

1. A method for measuring Troponin I in a sample with 1 pM limit of detection, comprising at least the following steps:
   a. providing a sample comprising Troponin I to be measured;
   b. contacting the sample with three monoclonal anti-Troponin I antibodies coupled to a labeled polymer coated iron oxide particle having a size of from 200 to 1000 nm;
   c. applying a first magnetic field in the direction of a sensor surface, thereby contacting the particles with a polyclonal anti-Troponin I antibody coupled to the sensor surface, thereby causing at least some of the particles to be bound to the sensor surface, wherein the polyclonal anti-Troponin I antibody binds to Troponin I at the same time as the monoclonal anti-Troponin I antibody;
   d. applying pulsed actuation by discontinuing the first magnetic field, thereby allowing unbound particles to move over the sensor surface, reapplying the first magnetic field, and discontinuing the first magnetic field, thereby increasing the number of particles bound to the sensor surface, and alternating the application of pulsed actuation with the application of magnetic pulses causing translational and rotational movement of the particles over the sensor surface, wherein the pulsed actuation and magnetic pulses are applied for less than five minutes; and e. applying a second magnetic field in a direction away from the sensor surface to remove unbound particles, and thereafter detecting the labeled polymer coated iron oxide particles on the sensor surface;

wherein the three monoclonal anti-Troponin I antibodies are clones A34500, 267, and 560.

2. The method according to claim 1, wherein the polyclonal anti-Troponin I antibody used is a goat polyclonal antibody.

3. The method according to claim 1, wherein the labeled polymer coated iron oxide particle is optically detected by Frustrated Total Internal Reflection (FTIR).

4. The method according to claim 1 wherein the labeled polymer coated iron oxide particle is magnetically detected.

5. The method according to claim 1, wherein the sample is from a patient suspected of myocardial infarction.

* * * * *